United States Patent
Hyde et al.

(10) Patent No.: US 8,396,672 B2
(45) Date of Patent: *Mar. 12, 2013

(54) FOOD CONTENT DETECTOR

(75) Inventors: Roderick A. Hyde, Redmond, WA (US); Muriel Y. Ishikawa, Livermore, CA (US); Jordin T. Kare, Seattle, WA (US); Eric C. Leuthardt, St. Louis, MO (US); Elizabeth A. Sweeney, Seattle, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 435 days.

This patent is subject to a terminal disclaimer.

(21) Appl. No.: 12/313,023

(22) Filed: Nov. 14, 2008

(65) Prior Publication Data

US 2010/0125178 A1    May 20, 2010

(51) Int. Cl.
*G01N 33/48* (2006.01)
(52) U.S. Cl. ........................................... 702/19
(58) Field of Classification Search ............. 702/19
See application file for complete search history.

(56) References Cited

U.S. PATENT DOCUMENTS

| | | | |
|---|---|---|---|
| 4,387,777 A | 6/1983 | Ash | |
| 5,299,356 A * | 4/1994 | Maxwell, III | 30/322 |
| 5,388,043 A | 2/1995 | Hettinger | |
| 5,454,721 A | 10/1995 | Kuch | |
| 6,236,001 B1 | 5/2001 | Shymko | |
| 6,404,838 B1 * | 6/2002 | Hall | 377/16 |
| 6,425,862 B1 | 7/2002 | Brown | |
| 6,850,861 B1 | 2/2005 | Faiola et al. | |
| 6,978,221 B1 | 12/2005 | Rudy | |
| 7,550,683 B2 | 6/2009 | Daughtry | |
| 2002/0027164 A1 | 3/2002 | Mault et al. | |
| 2002/0047867 A1 | 4/2002 | Mault et al. | |
| 2002/0124017 A1 | 9/2002 | Mault | |
| 2003/0076983 A1 | 4/2003 | Cox | |
| 2005/0011367 A1 | 1/2005 | Crow | |
| 2005/0184148 A1 * | 8/2005 | Perlman | 235/383 |
| 2005/0187148 A1 | 8/2005 | Naoe et al. | |
| 2006/0036395 A1 | 2/2006 | Shaya et al. | |
| 2007/0028453 A1 | 2/2007 | Crow | |
| 2007/0098856 A1 | 5/2007 | LePine | |
| 2008/0060853 A1 | 3/2008 | Davidson et al. | |

FOREIGN PATENT DOCUMENTS

WO   WO2005/006924   1/2005

* cited by examiner

*Primary Examiner* — Aditya Bhat

(74) *Attorney, Agent, or Firm* — Suiter Swantz pc llo

(57) ABSTRACT

A system may include utensil means for portioning a foodstuff into a first portion and a second portion, a means for detecting a first portion size for the first portion with the utensil means, a means for detecting a second portion size for the second portion with the utensil means, and a means for determining a cumulative amount of portioned foodstuff based upon the first portion size and the second portion size.

45 Claims, 10 Drawing Sheets

256 DETERMINATION MODULE

258 SENSOR
- 259 CALORIMETER
- 260 CONDUCTIVITY SENSOR
- 261 ELECTRICAL LEAD
- 262 ENZYMATIC SENSOR
- 263 BIO SENSOR
- 264 CHEMICAL SENSOR
- 265 MICROCHIP SENSOR
- 266 ENZYME-LINKED ASSAY SENSOR
- 267 IR SPECTROSCOPY SENSOR
- 268 NMR SENSOR
- 269 OPTICAL SENSOR
- 270 PERMITTIVITY SENSOR
- 271 GAS SENSOR
- 272 RF SENSOR
- 273 ELECTRONIC NOSE SENSOR
- 274 ELECTRONIC TONGUE SENSOR
- 275 MULTI-FREQUENCY RF SENSOR
- 276 CANTILEVER SENSOR
- 277 ACOUSTIC WAVE SENSOR
- 278 PIEZOELECTRIC SENSOR
- 279 RESPONSIVE POLYMER-BASED SENSOR
- 280 QUARTZ MICROBALANCE SENSOR
- 281 METAL OXIDE SENSOR
- 282 XRF SENSOR
- 283 NUCLEIC ACID-BASED SENSOR
- 284 REGENERABLE SENSOR

286 RECEIVER
- 288 BARCODE READER
- 290 DATABASE
- 292 LABEL READER
- 294 MEAL-SPECIFIC ASSOCIATION
- 296 USER INPUT

FIG. 3

FOOD CONTENT DETECTOR

BACKGROUND

Tools and utensils for portioning and consuming foods are ever-present. Although the form factor of such tools/utensils may vary, their basic function is generally the same (e.g., serving food and moving food from plate to mouth). Many people would like information about the food that they consume utilizing such tools/utensils.

SUMMARY

In one aspect, a system includes but is not limited to utensil means for portioning a foodstuff into a first portion and a second portion, a means for detecting a first portion size for the first portion with the utensil means, a means for detecting a second portion size for the second portion with the utensil means, and a means for determining a cumulative amount of portioned foodstuff based upon the first portion size and the second portion size. In addition to the foregoing, other system aspects are described in the claims, drawings, and text forming a part of the present disclosure.

In another aspect, a system includes but is not limited to a means for portioning a foodstuff into a first portion and a second portion, a means for detecting a first portion size for the first portion with the portioning means, a means for detecting a second portion size for the second portion with the portioning means, a means for determining a cumulative amount of portioned foodstuff based upon the first portion size and the second portion size, and a means for determining a nutritional parameter for the portioned foodstuff. In addition to the foregoing, other system aspects are described in the claims, drawings, and text forming a part of the present disclosure.

In a further aspect, a system includes but is not limited to a means for presenting a portioned foodstuff for consumption by at least one user, a means for detecting at least one compound in the portioned foodstuff, and a means for reporting information concerning the at least one compound in the portioned foodstuff. In addition to the foregoing, other system aspects are described in the claims, drawings, and text forming a part of the present disclosure.

In a still further aspect, a system includes but is not limited to utensil means for portioning a foodstuff into a first portion and a second portion, a means for detecting a first nutritional content for the first portion with the utensil means, a means for detecting a second nutritional content for the second portion with the utensil means, and a means for determining a cumulative amount of nutritional content based upon the first nutritional content and the second nutritional content. In addition to the foregoing, other system aspects are described in the claims, drawings, and text forming a part of the present disclosure.

In another aspect, a system includes but is not limited to a means for presenting a portioned foodstuff for consumption by at least one user, a means for detecting a portion size for the portioned foodstuff for consumption by the at least one user, and a means for determining a nutritional parameter for the portioned foodstuff. In addition to the foregoing, other system aspects are described in the claims, drawings, and text forming a part of the present disclosure.

In addition to the foregoing, various other method and/or system and/or program product aspects are set forth and described in the teachings such as text (e.g., claims and/or detailed description) and/or drawings of the present disclosure.

A device includes a utensil for portioning a foodstuff into a first portion and a second portion, a detector coupled to the utensil for detecting a first portion size for the first portion and detecting a second portion size for the second portion, and a processor coupled to the detector for determining a cumulative amount of portioned foodstuff based upon the first portion size and the second portion size.

A device includes a tool for portioning a foodstuff into a first portion and a second portion, a detector coupled to the tool for detecting a first portion size for the first portion and detecting a second portion size for the second portion, a processor coupled to the detector for determining a cumulative amount of portioned foodstuff based upon the first portion size and the second portion size, and a determination module coupled to the tool for determining a nutritional parameter for the portioned foodstuff.

A device includes a tool for presenting a portioned foodstuff for consumption by at least one user, a sensor coupled to the tool for detecting at least one compound in the portioned foodstuff, and a reporter coupled to the sensor for reporting information concerning the at least one compound in the portioned foodstuff.

A device includes a utensil for portioning a foodstuff into a first portion and a second portion, a detector coupled to the utensil for detecting a first nutritional content for the first portion and detecting a second nutritional content for the second portion, and a processor coupled to the detector for determining a cumulative amount of nutritional content based upon the first nutritional content and the second nutritional content.

A device includes a tool for presenting a portioned foodstuff for consumption by at least one user, a detector coupled to the tool for detecting a portion size for the portioned foodstuff for consumption by the at least one user, and a determination module coupled to the tool for determining a nutritional parameter for the portioned foodstuff.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 3 is a schematic of a determination module for the device illustrated in FIG. 2.

DETAILED DESCRIPTION

Figure 1:
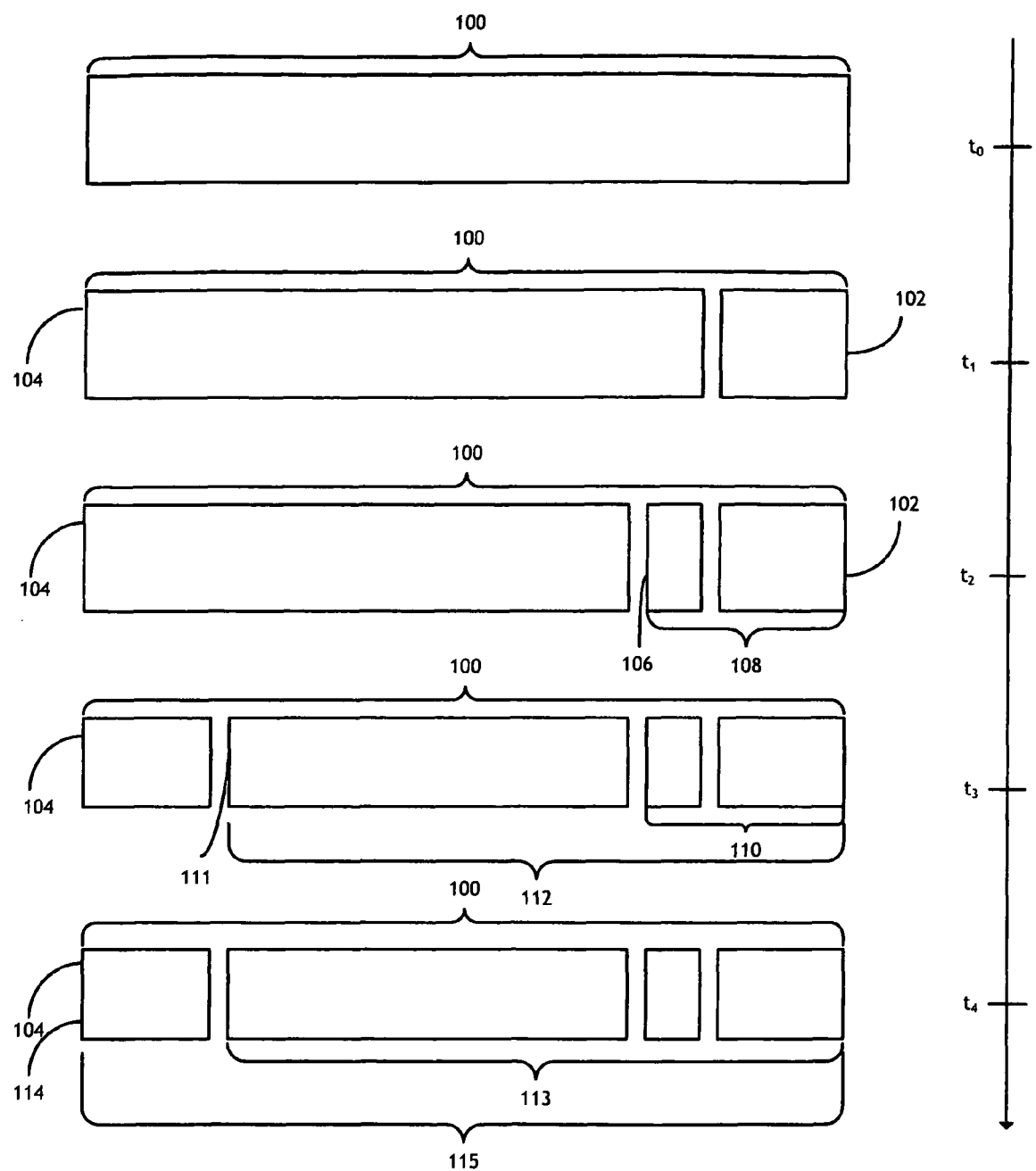
FIG. 1 is a schematic illustrating a foodstuff portioned into first and second portions over a period of time spanning from $t_0$ to $t_4$.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring now to FIG. 1, a foodstuff 100 is portioned into first and second portions over a period of time spanning from $t_0$ to $t_4$. Portioning includes dividing the foodstuff into at least bite-sized or serving-sized portions. At time $t_0$, the foodstuff 100 is presented. At time $t_1$, the foodstuff 100 is portioned into a first portion 102 having a first portion size, by separating the first portion 102 from the remaining foodstuff 104. At time $t_2$, the foodstuff 100 is portioned into a second portion 106 having a second portion size, by separating the second portion 106 from the remaining foodstuff 104. Together, the first portion 102 and the second portion 106 comprise a cumulative amount of portioned foodstuff 108 at time $t_2$. The cumulative amount of portioned foodstuff 108 is determined based upon the first portion size and the second portion size.

Next, the first portion 102 and the second portion 106, which comprise the cumulative amount of portioned foodstuff 108 at time $t_2$, are combined to represent a first portion 110 at time $t_3$. At time $t_3$, the foodstuff 100 is further portioned into a second portion 111, by separating the second portion 111 from the remaining foodstuff 104. Together, the first portion 110 and the second portion 111 comprise a cumulative amount of portioned foodstuff 112 at time $t_3$.

This may be repeated until the foodstuff 100 has been fully portioned. For instance, the first portion 110 and the second portion 111 are combined to represent a first portion 113 at time $t_4$. At time $t_4$, the foodstuff 100 is further portioned into a second portion 114, by designating the remaining foodstuff 104 as the second portion 114. Together, the first portion 113 and the second portion 114 comprise a cumulative amount of portioned foodstuff 115 at time $t_4$.

Figure 2:
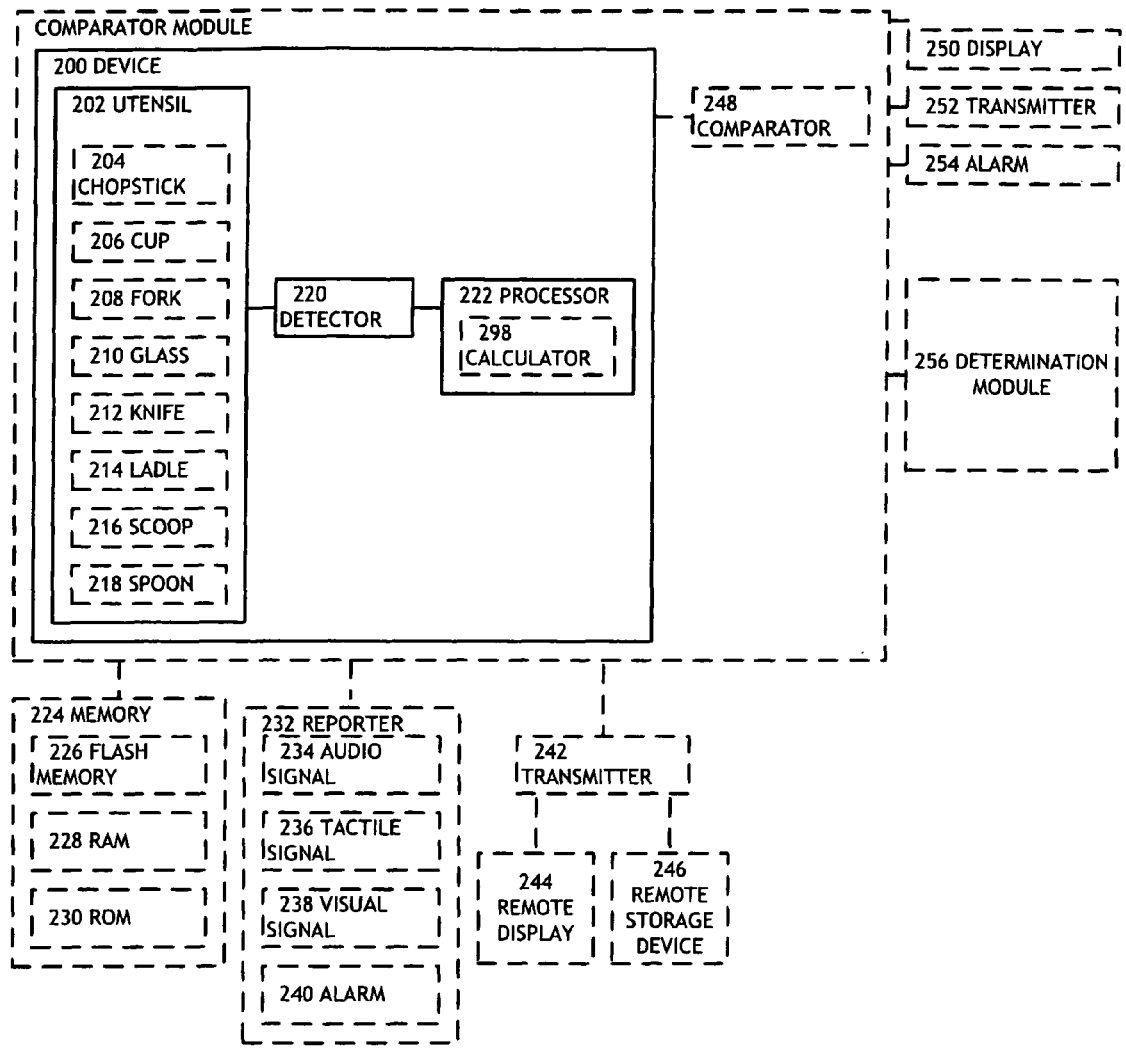
FIG. 2 is a schematic of a device for portioning the foodstuff illustrated in FIG. 1.

Referring now to FIGS. 2 and 3, a device 200 for portioning the foodstuff 100 (FIG. 1) is described. The device 200 includes an eating/serving utensil 202 for portioning the foodstuff into the first portion, e.g., 102, 110 or 113 (FIG. 1) and the second portion, e.g., 106, 111 or 114 (FIG. 1). The utensil 202 may comprise an eating instrument/implement that goes in the mouth (e.g., an eating instrument for moving food from plate to mouth). Without limitation, the utensil 202 may comprise one or more of a chopstick 204, a cup 206, a fork 208, a glass 210, a knife 212, a ladle 214, a scoop 216, or a spoon 218. For example, the utensil 202 may comprise an ice cream scoop. The utensil 202 is coupled to a detector 220 for detecting a first portion size for the first portion and detecting a second portion size for the second portion. The detector 220 may comprise an onboard mass sensor, volume sensor, or weight sensor.

The detector 220 may comprise a strain gauge, i.e., a device that responds to mechanical strain in a measurable way, such as by changing the resistance of a material. The strain gauge may be connected to the utensil 202. By correlating the measurable response of the strain gauge to variations in mass or weight supported by the utensil 202, the detector 220 may be calibrated for determining the mass or weight of a portion of the foodstuff supported by the utensil 202. Further, the detector 220 may comprise a density sensor, such as an ultrasonic sensor, or the like, for detecting the density of the foodstuff. By determining the density of a foodstuff supported by the utensil 202, a volume for the foodstuff may also be detected (e.g., by detecting a mass of the foodstuff and then utilizing a density for the foodstuff to calculate a volume for the foodstuff).

The detector 220 may comprise an imager, i.e., a camera or another device for capturing one or more images of a foodstuff. The imager may be focused on the utensil 202. By correlating images of foodstuff or other materials supported by the utensil 202 to variations in volume supported by the utensil 202 (e.g., by measuring a level of the foodstuff relative to the utensil 202), the detector 220 may be calibrated for determining the volume of a portion of the foodstuff supported by the utensil 202. Further, the detector 220 may comprise a density sensor, such as the ultrasonic sensor for detecting the density of the foodstuff. By determining the density of a foodstuff supported by the utensil 202, a mass or weight for the foodstuff may also be detected (e.g., by detecting a volume of the foodstuff and then utilizing a density for the foodstuff to calculate a mass or weight for the foodstuff).

Thus, the detector 220 may detect the first portion size and the second portion size by one or more of mass, volume, and weight. For instance, each portion size may be detected as a change in mass for the utensil 202. By comparing a first mass detected for a lifted/pre-ingested utensil 202 (i.e., a utensil 202 supporting a portion of the foodstuff) to a second mass detected for the bare/post-ingested utensil 202, a portion sized by mass can be detected for an amount of the foodstuff ingested. Further, the detector 220 may utilize one or more acceleration measurements (e.g., from an accelerometer) to account for inertial effects when making a mass determination for a portion of the foodstuff. Each portion size may be detected as a change in volume for the utensil 202. For example, by comparing a first volume detected for a lifted/pre-ingested utensil 202 (i.e., a utensil 202 supporting a portion of the foodstuff) to a second volume detected for the bare/post-ingested utensil 202, a portion sized by volume can be detected for an amount of the foodstuff ingested.

The detector 220 is coupled to a processor 222 for determining the cumulative amount of portioned foodstuff 108 (FIG. 1) based upon the first portion size and the second portion size. For instance, a user may separate a first portion 102 from a remaining portion 104 of foodstuff 100 (see FIG. 1). The first portion 102 may comprise a quantity of food having a first portion size of 15 grams (g). Then, the user may separate a second portion 106 from the remaining portion 104 of foodstuff 100. The second portion 106 may comprise a second quantity of food having a second portion size of 13 g. The processor 222 may add the first portion size of 15 g to the second portion size of 13 g for a cumulative amount of portioned foodstuff 108 comprising 28 g. In this manner, the processor 222 may be utilized to provide a positive accumulation of foodstuff.

In another example, a user may separate a first portion 102 comprising a quantity of food having a first portion size of 14 g from a remaining portion 104 of foodstuff 100. Then, the user may separate a second portion 106 comprising a quantity of food having a second portion size of 16 g from the remaining portion 104 of foodstuff 100. The processor 222 may subtract the first portion size of 14 g and the second portion size of 16 g from a starting amount (such as 100 g) for a cumulative amount of portioned foodstuff comprising 30 g, which may be subtracted from the 100 g, leaving a balance of 70 g. In this manner, the processor 222 may be utilized to provide a negative accumulation of foodstuff.

The device 200 may comprise a determination module 256 for determining a nutritional parameter for the portioned foodstuff. In an embodiment, the determination module 256 may be configured to determine an energy density for the portioned foodstuff. More specifically, the energy density for the portioned foodstuff may be determined in terms of a calorie density. In an embodiment, the determination module 256 may be configured to determine a component concentration for the portioned foodstuff. The determination module 256 for determining the component concentration may be capable of determining at least one of a carbohydrate, a monosaccharide, a disaccharide, an oligosaccharide, a polysaccharide, a cellulose component, a fiber component, a sugar component, a dairy component, a fat, a saturated fat, an unsaturated fat, a polyunsaturated fat, a trans fat, a cholesterol component, a lipoprotein, a mineral, a peanut component, a protein, a salt, a triglyceride, or a vitamin. It will be appreciated that this list of components is not meant to be exclusive, and it is contemplated that a wide variety of other ingredients in various concentrations may also be detected. In an embodiment, the determination module 256 may be configured to determine the nutritional parameter on at least one of a per-mass basis, a per-volume basis, or a per-weight basis.

The determination module 256 for determining the nutritional parameter for the portioned foodstuff may comprise a sensor 258 for measuring the nutritional parameter for the portioned foodstuff. The sensor 258 may comprise at least one of a calorimeter 259, a conductivity sensor 260, an electrical lead 261, an enzymatic sensor 262, a biosensor 263, a chemical sensor 264, a microchip sensor 265, an Enzyme-Linked Assay sensor 266 (e.g., an Enzyme-Linked Immunosorbent Assay (ELISA) sensor), an infrared (IR) spectroscopy sensor 267, a Nuclear Magnetic Resonance (NMR) sensor 268, an optical sensor 269, a permittivity sensor 270, a gas sensor 271, a Radio Frequency (RF) sensor 272, an electronic nose sensor 273, an electronic tongue sensor 274, a multi-frequency RF sensor 275, a cantilever sensor 276, an acoustic wave sensor 277, a piezoelectric sensor 278, a responsive polymer-based sensor 279, a quartz microbalance sensor 280, a metal oxide sensor 281, an X-ray Fluorescence (XRF) sensor 282, a nucleic acid-based sensor 283 (e.g., a DNA-, RNA-, or aptamer-based sensor), or a regenerable sensor 284. For example, the calorimeter 259 may be utilized for measuring a calorie density for the portioned foodstuff. In an example, the biosensor 263 may be utilized for detecting/measuring a peanut component in the portioned foodstuff.

The determination module 256 for determining the nutritional parameter for the portioned foodstuff may also comprise a receiver 286 for receiving the nutritional parameter for the portioned foodstuff. The receiver 286 may comprise at least one of a barcode reader 288, a database 290, a label reader 292, a meal-specific association 294, or a user input 296. For instance, a container of the foodstuff may comprise a barcode with one or more nutritional parameters embedded in the barcode or associated with the barcode (e.g., a prepackaged foodstuff may include a tray having a barcode). The receiver 286 comprising a barcode reader 288 may be configured to read a nutritional parameter embedded in the barcode. Alternatively, the determination module 256 may be configured to took up a nutritional parameter by retrieving data indicated by the barcode. In another example, the receiver 286 may be configured to receive one or more user inputs 296 specifying the nutritional parameter of the portioned foodstuff.

It is contemplated that the processor 222 coupled to the detector 220 for determining the cumulative amount of portioned foodstuff based upon the first portion size and the second portion size may comprise a calculator 298. The calculator 298 may be utilized by the processor 222 for calculating a nutritional content for the portioned foodstuff. In one embodiment, the nutritional content may be calculated by the calculator 298 utilizing the nutritional parameter determined by the determination module 256 for the portioned foodstuff and the cumulative amount of the portioned foodstuff determined by the processor 222. For instance, the nutritional content may be calculated based on the energy density determined by the determination module 256 for the portioned foodstuff and the cumulative amount of the portioned foodstuff. If the energy density determined by the determination module 256 for the portioned foodstuff is, for example, 5 calories per 1 g, and the cumulative amount of the portioned foodstuff consumed by the user up to this point is 50 g, the calculator 298 may calculate the nutritional content in terms of calorie density as 250 calories. In another example, the nutritional content may be calculated based on the component concentration determined by the determination module 256 for the portioned foodstuff and the cumulative amount of the portioned foodstuff.

It is contemplated that the device 200 may comprise a memory 224 for storing the cumulative amount or the nutritional content of the portioned foodstuff determined by the processor 222. The memory 224 may comprise one or more of a flash memory 226, a random access memory (RAM) 228, or a read-only memory (ROM) 230. The processor 222 may access or update the cumulative amount and the nutritional content of the portioned foodstuff stored in the memory 224 during portioning operations performed by the device 200. For example, as the user separates the second portion 106 from the remaining portion 104 of foodstuff 100, the processor 222 may retrieve the cumulative amount of portioned foodstuff 108 currently stored in the memory 226. The processor 222 may then determine a new cumulative amount based on the cumulative amount of portioned foodstuff 108 retrieved from the memory 226 and the second portion size of the second portion 106. The processor 222 may update the cumulative amount of portioned foodstuff 108 stored in the memory 226 to reflect the new cumulative amount determined. The nutritional content of the portioned foodstuff stored in the memory 224 may also be accessed and updated accordingly.

The device 200 may comprise a reporter 232 for reporting the cumulative amount or the nutritional content of the portioned foodstuff determined by the processor 222. The reporter 232 may provide one or more of an audio signal 234, a tactile signal 236, or a visual signal 238. For instance, the reporter 232 may be configured with a display device (e.g., an LCD screen) for delivering one or more visual signals 238 to the user indicating the cumulative amount of portioned foodstuff 108 consumed by the user. It is understood that audio signals, tactile signals, visual signals, or a combination of such signals may be utilized by the reporter 232. In one embodiment, an LCD screen may be configured to provide information about the amount of foodstuff, such as a smiley face in the case of a desirable quantity that has been ingested. In another embodiment, a speaker may be configured to provide one or more tones, such as a warning signal/alarm in the case of an undesirable quantity of ingested foodstuff.

The reporter 232 may be configured to report when the cumulative amount or the nutritional content of the portioned foodstuff has reached a target amount. In one embodiment, the reporter 232 may comprise an alarm 240 for alerting the user when the target amount is reached. For example, the user may configure the target amount to be 500 g by weight. Thus, the alarm 240 may alert the user once the cumulative amount of portioned foodstuff determined by the processor 222 reaches or exceeds the target amount of 500 g. Such alert may be in forms of an audio alert, a tactile alert, a visual alert, or a combination of such alerts. In another example, the user may configure the target amount to be 800 calories. Thus, the alarm 240 may alert the user once the nutritional content of the portioned foodstuff determined by the processor 222 reaches or exceeds the target amount of 800 calories.

The device 200 may further comprise a transmitter 242 for transmitting the cumulative amount or the nutritional content of the portioned foodstuff to a remote device. The transmitter 242 may utilize various communication technologies for data transmission. Such technologies may include, but are not limited to, radio transmission, Bluetooth transmission, Wi-Fi technology, infrared, and other wireless communication technologies. The remote device receiving the cumulative amount or the nutritional content of the portioned foodstuff may be utilized for various purposes. In one embodiment, the transmitter 242 may transmit the cumulative amount or the nutritional content of the portioned foodstuff to a remote display 244. The remote display 244 may be, for example, an external monitor capable of displaying information comprising the cumulative amount or the nutritional content of the portioned foodstuff. In another embodiment, the transmitter 242 may transmit the cumulative amount or the nutritional content of the portioned foodstuff to a remote storage device 246. The remote storage device 246 may be, for example, a computer hard drive for logging daily consumption records for the user.

The device 200 may also comprise a comparator 248 for comparing the cumulative amount or the nutritional content of the portioned foodstuff to a target amount. For instance, the comparator 248 may compare the cumulative amount or the nutritional content of the portioned foodstuff against the target amount when the second portion is separated from the remaining foodstuff (e.g., when the user imbibes a subsequent portion from the remaining foodstuff). In one embodiment, a comparison result (a representation of the comparison) may be reported on a display 250. In another embodiment, a transmitter 252 may be utilized to transmit the representation of the comparison to a remote device. In still another embodiment, an alarm 254 may alert the user regarding the comparison; for example, when the cumulative amount or the nutritional content of the portioned foodstuff approaches the target amount.

The target amount may be, for example, a pre-defined value indicating a minimum amount of calories required after ingesting a particular drug. In such cases, the target amount may be an essential requirement set by the user who ingested the drug, a doctor, or another healthcare professional. In another example, the user may set the target amount to be a goal amount that the user is trying to achieve. The goal amount may be set as a maximum calorie amount the user is trying not to exceed for achieving a dietary goal. Alternatively, a minimum amount of a particular ingredient (e.g., a vitamin or a mineral, such as iron) to be ingested may also be set as a goal amount.

It is understood that the target/goal amount may be tracked through positive or negative accumulation of foodstuff. It is also understood that the target/goal amount may be associated with a particular dietary program. For example, a dietary program may utilize a point value system to assign point values to a foodstuff ingested by a user (a participant of the dietary program) based on one or more nutritional parameters for the foodstuff. Such nutritional parameters may include, for example, one or more of calorie density, fat content, or dietary fiber content. For instance, the point value system may assign one point for every 100 calories and one point for every gram of fat contained in the foodstuff. The dietary program may recommend/set a certain number of points to be ingested within a specific period of time. For instance, the dietary program may recommend a participant to ingest up to a total of 20 points per day. The target/goal amount may be configured to adapt and facilitate such point value systems.

Figure 4:
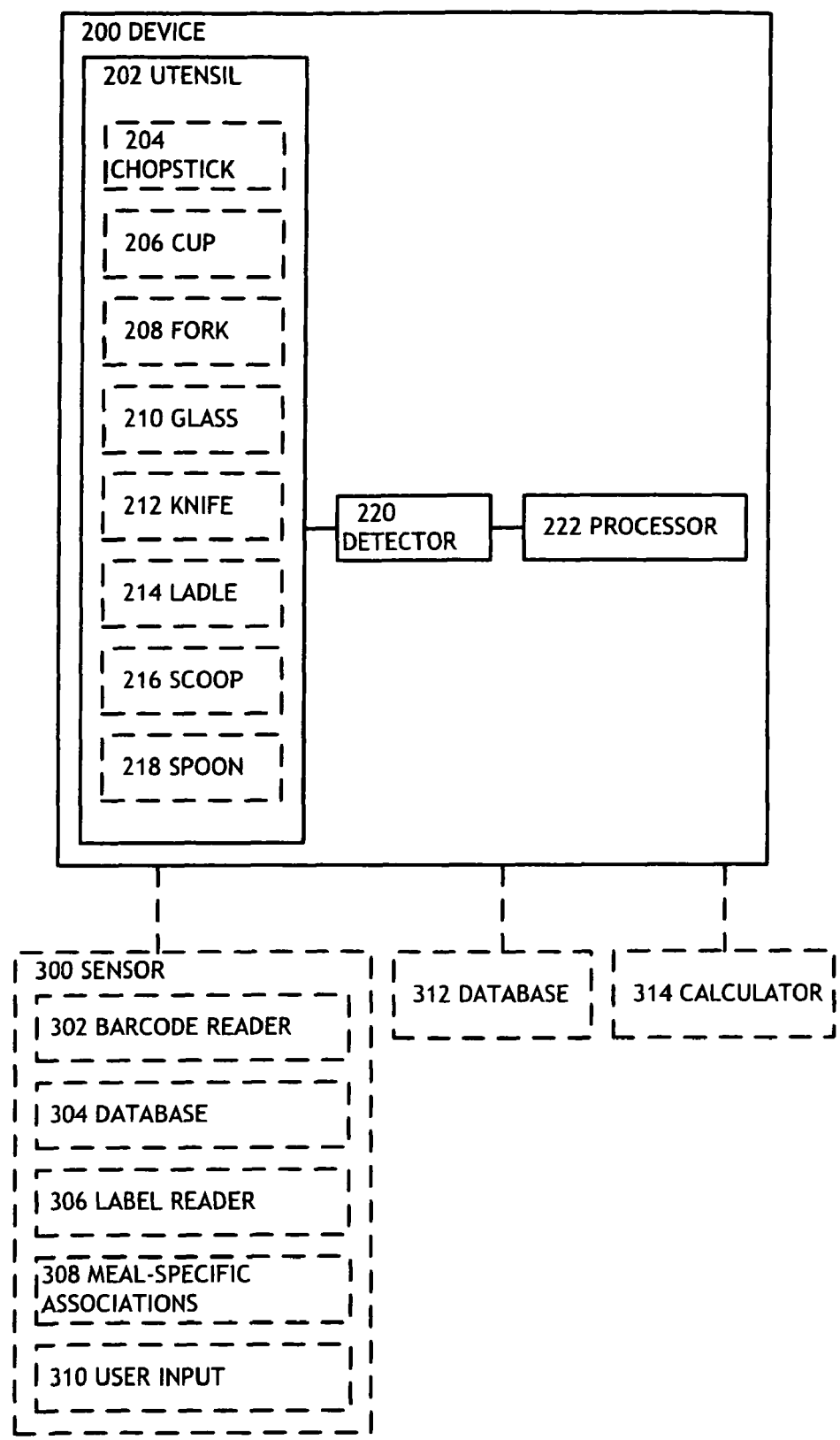
FIG. 4 is another schematic of the device illustrated in FIG. 2.

Referring now to FIG. 4, the device 200 may comprise a sensor 300, a database 312, and a calculator 314. The sensor 300 may be utilized for determining a type of the portioned foodstuff. The sensor 300 may comprise at least one of a barcode reader 302, a database 304, a label reader 306, a meal-specific association 308, or a user input 310. For instance, a container of foodstuff may comprise a barcode indicating the type of the foodstuff (e.g., a fruit, a vegetable, or a meat). The sensor 300 comprising a barcode reader 302 may be configured to read the barcode and determine the type of the foodstuff. Once the type of the foodstuff is determined, the device 200 may refer to the database 312 to obtain a stored nutritional parameter for this type of foodstuff. For example, if the sensor 300 determines that the portioned foodstuff is or contains banana, the device 200 may then obtain the stored nutritional parameter for banana from the database 312. The calculator 314 may be utilized for calculating a nutritional content for the portioned foodstuff utilizing the stored nutritional parameter for the portioned foodstuff and the cumulative amount of the portioned foodstuff. In the above example, the calculator 314 may calculate the nutritional content for the banana based on the stored nutritional parameter obtained from the database 312 and the cumulative amount consumed by the user up to this point.

Figure 5:
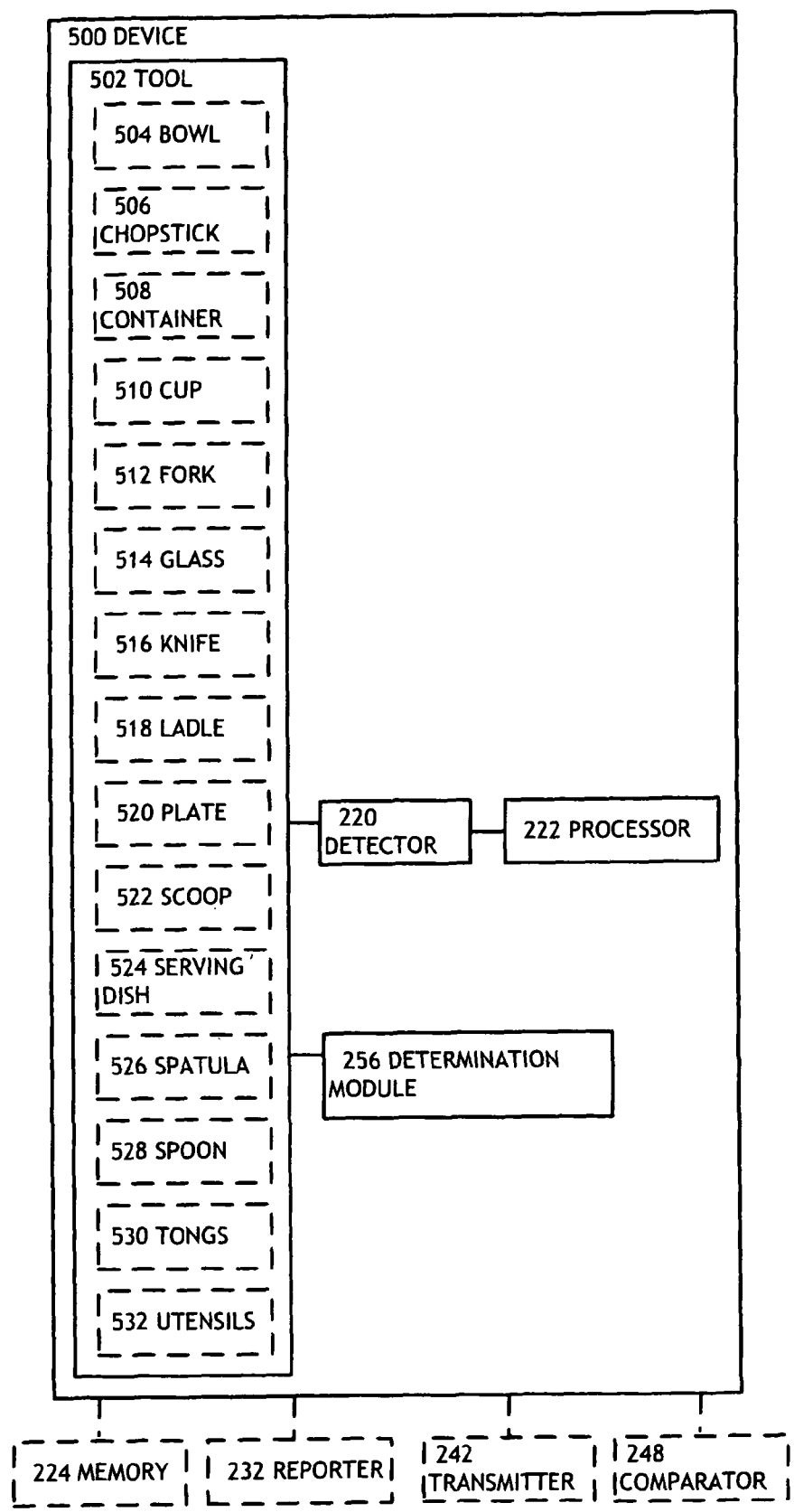
FIG. 5 is a schematic of another device for portioning a foodstuff.

Referring now to FIG. 5, a device 500 for portioning a foodstuff is described. The device 500 includes a tool 502 for portioning the foodstuff into a first portion and a second portion. The tool 502 may comprise a container for carrying/serving the foodstuff or an eating instrument/implement that goes in the mouth. The tool 502 may comprise one or more of a bowl 504, a chopstick 506, a container 508, a cup 510, a fork 512, a glass 514, a knife 516, a ladle 518, a plate 520, a scoop 522, a serving dish 524, a spatula 526, a spoon 528, tongs 530, or a utensil 532. For example, the tool 502 may comprise a salad container. The tool 502 is coupled to detector 220 for detecting a first portion size for the first portion and detecting a second portion size for the second portion (as previously described). The detector 220 is coupled to processor 222 for determining the cumulative amount of portioned foodstuff based upon the first portion size and the second portion size (as previously described). The tool 502 is also coupled to determination module 256 for determining a nutritional parameter for the portioned foodstuff (as previously described).

It is contemplated that the device 500 may comprise memory 224 for storing the cumulative amount or the nutritional content of the portioned foodstuff determined by the tool 502 (as described above). The device 500 may also comprise reporter 232 for reporting the cumulative amount or the nutritional content of the portioned foodstuff determined (as previously described). In addition, the device 500 may comprise transmitter 242 for transmitting the cumulative amount or the nutritional content of the portioned foodstuff to a remote device (as described above).

The device 500 may further comprise comparator 248 for comparing the cumulative amount or the nutritional content of the portioned foodstuff to a target amount (as described above). In one embodiment, a comparison result (a representation of the comparison) may be reported on the display 250, as previously described. In another embodiment, the transmitter 252 may be utilized to transmit the representation of the comparison to a remote device, as previously described. In still another embodiment, the alarm 254 may alert the user regarding the comparison, as previously described. For example, when the cumulative amount or the nutritional content of the portioned foodstuff approaches the target amount, the alarm 254 may sound to alert the user results of the comparison (e.g., when approximately 95% of a desirable number of calories has been consumed).

Figure 6:
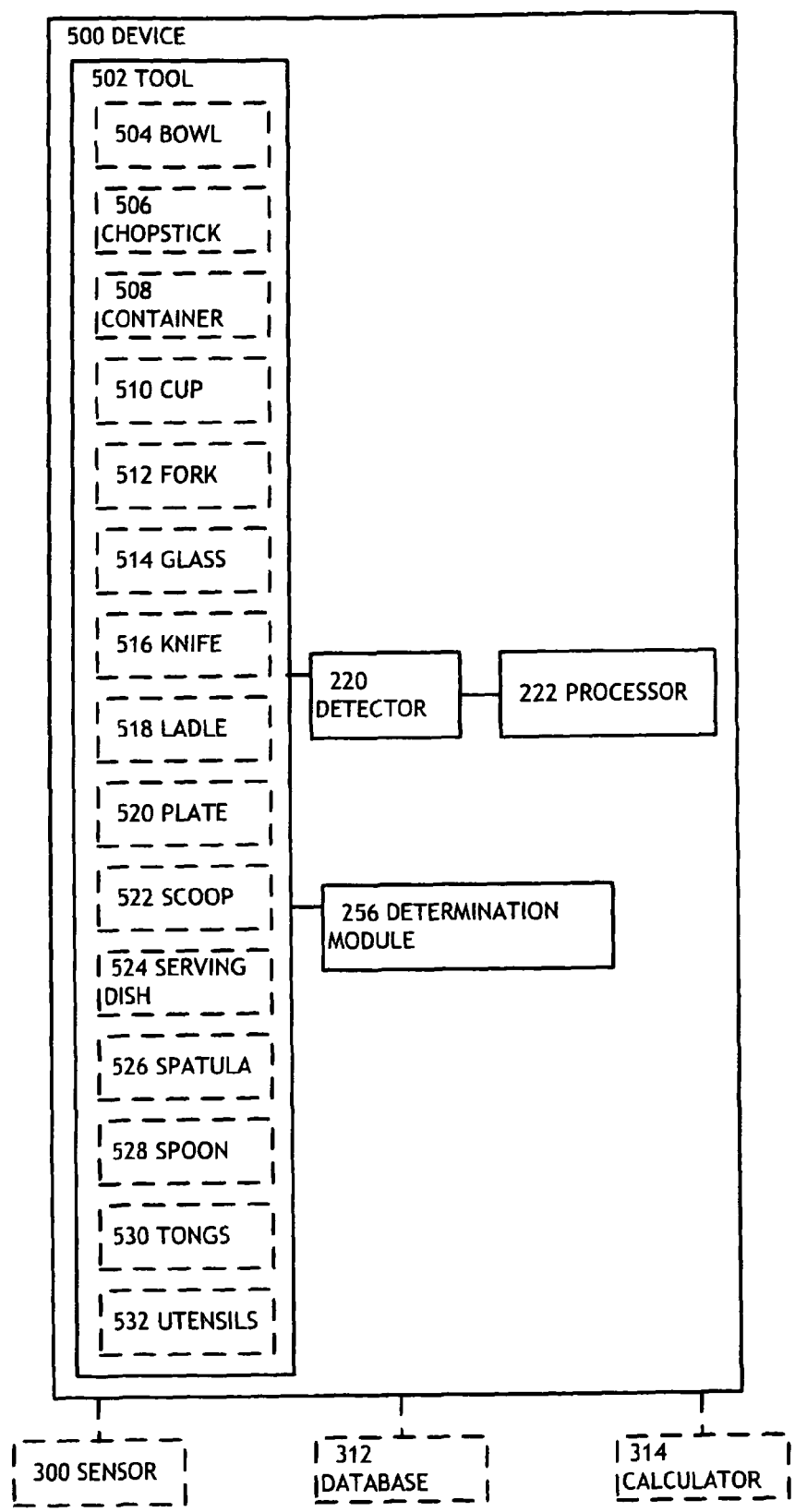
FIG. 6 is another schematic of the device illustrated in FIG. 5.

Referring now to FIG. 6, the device 500 may comprise sensor 300 for determining a type of the portioned foodstuff (as previously described). Once the type of the foodstuff is determined, the device 500 may refer to database 312 to obtain a stored nutritional parameter for this type of foodstuff (as described above) The device 500 may also include calculator 314 for calculating a nutritional content for the portioned foodstuff (as previously described) For example, the calculator 314 may calculate the nutritional content for the foodstuff based on the stored nutritional parameter obtained from the database 312 and a cumulative amount consumed by the user.

Figure 7:
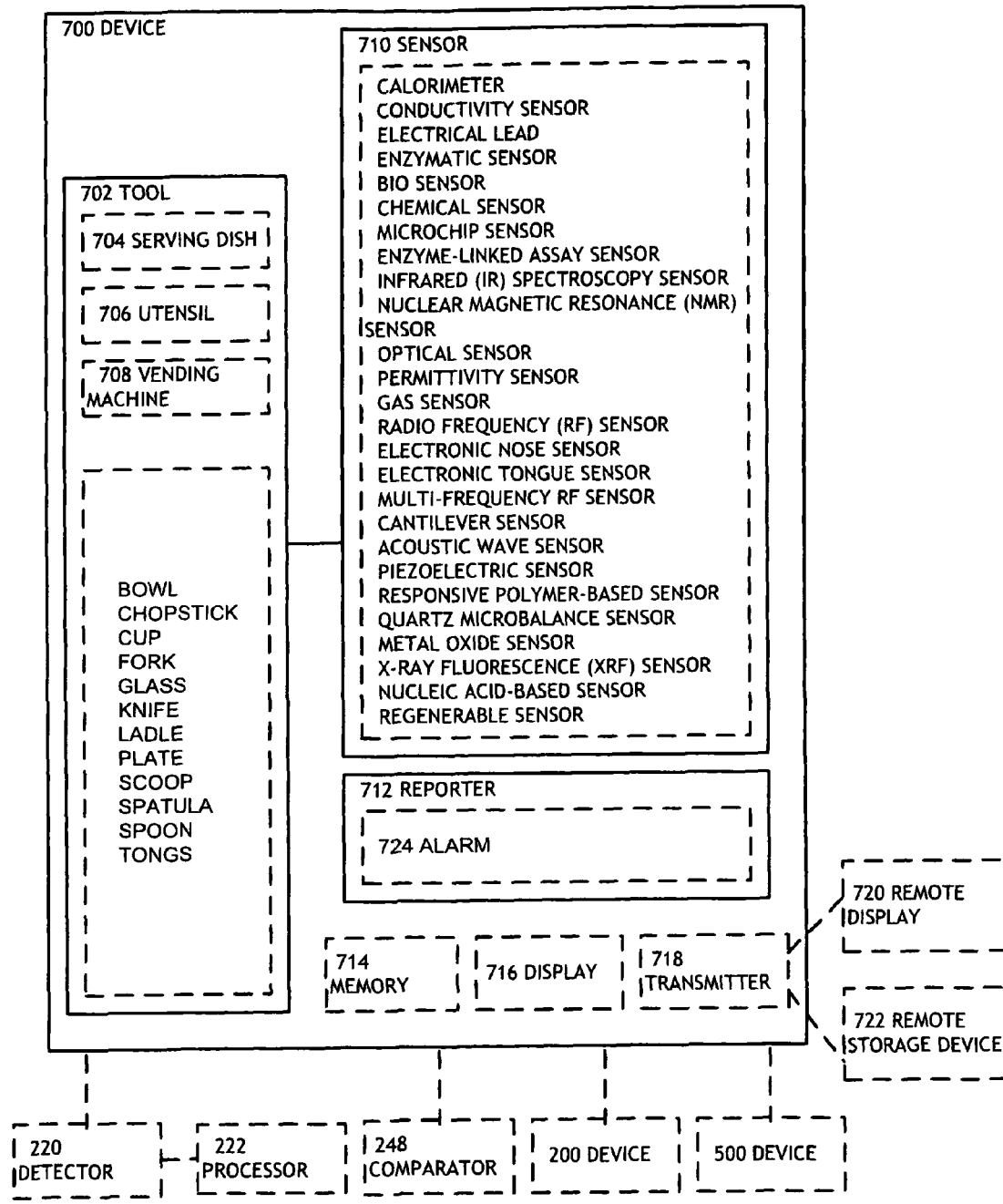
FIG. 7 is a schematic of another device for portioning a foodstuff.

Referring now to FIG. 7, a device 700 for presenting a portioned foodstuff is described. The device 700 includes a tool 702 for presenting the portioned foodstuff for consumption by at least one user. The tool 702 may comprise a container for presenting/serving the foodstuff or an eating instrument/implement that goes in the mouth. The tool 702 may comprise one or more of a serving dish 704, a utensil 706, or a vending machine 708. For example, the tool 702 may comprise one or more of a bowl, a chopstick, a cup, a fork, a glass, a knife, a ladle, a plate, a scoop, a spatula, a spoon, or tongs. The tool 702 is coupled to a sensor 710 for detecting at least one compound in the portioned foodstuff. In one embodiment, the sensor 710 may be configured for sensing one or more of a carbohydrate, a monosaccharide, a disaccharide, an oligosaccharide, a polysaccharide, a cellulose component, a fiber component, a sugar component, a dairy component, a fat, a saturated fat, an unsaturated fat, a polyunsaturated fat, a trans fat, a cholesterol component, a lipoprotein, a mineral, a peanut component, a protein, a salt, a triglyceride, or a vitamin. In another embodiment, the sensor 710 may be configured for sensing a marker indicating the presence of at least one of a carbohydrate, a monosaccharide, a disaccharide, an oligosaccharide, a polysaccharide, a cellulose component, a fiber component, a sugar component, a dairy component, a fat, a saturated fat, an unsaturated fat, a polyunsaturated fat, a trans fat, a cholesterol component, a lipoprotein, a mineral, a peanut component, a protein, a salt, a triglyceride, or a vitamin. For example, a foodstuff being sold in a vending machine 708 may comprise a marker indicating the vitamin content of the foodstuff. The vending machine 708 may be configured to sense the marker to obtain the vitamin content information of the foodstuff. In another example, the sensor 710 may be utilized for sensing a marker of a foodstuff which may indicate the presence of one or more of an allergen, a bacterium, a culturally prohibited ingredient, a drug, a pollutant, a genetically modified compound, a toxin, or a byproduct of a toxin. For example, the presence of a drug or a pollutant may be indicated by the presence of a pesticide, a growth factor, a hormone, a hormone mimetic, or an antibiotic. It will be appreciated that this list provides examples of various drugs and pollutants and is not meant to be restrictive of the present disclosure. Various other drugs and pollutants may be detected as well.

In one embodiment, the sensor 710 may comprise one or more of a calorimeter, a conductivity sensor, an electrical lead, an enzymatic sensor, a biosensor, a chemical sensor, a microchip sensor, an Enzyme-Linked Assay sensor (e.g., an Enzyme-Linked Immunosorbent Assay (ELISA) sensor), an infrared (IR) spectroscopy sensor, a Nuclear Magnetic Resonance (NMR) sensor, an optical sensor, a permittivity sensor, a gas sensor, a Radio Frequency (RF) sensor, an electronic nose sensor, an electronic tongue sensor, a multi-frequency RF sensor, a cantilever sensor, an acoustic wave sensor, a piezoelectric sensor, a responsive polymer-based sensor, a quartz microbalance sensor, a metal oxide sensor, an X-ray Fluorescence (XRF) sensor, a nucleic acid-based sensor (e.g., a DNA-, RNA-, or aptamer-based sensor), or a regenerable sensor. For example, the sensor 710 may comprise a biosensor, for example one comprising in part a recognition element such as an antibody, for sensing the presence of protein in the foodstuff. In another example, the sensor 710 may be configured for sensing one or more of an allergen, a bacterium, a culturally prohibited ingredient, a drug, a pollutant, a genetically modified compound, a toxin, or a byproduct of a toxin. In addition, the sensor 710 may also be configured for sensing one or more of an animal product, *Clostridium botulinum*, a dairy-based compound, a dairy product, *Escherichia coli*, a peanut product, a nut product, or pork. It is contemplated that animal products may include meats, organs, or any compound naturally found in species from the animal kingdom but not commonly found in the plant kingdom. For example, animal products may include animal cells, proteins, antibodies, and the like. It will be appreciated that a nut product may include a tree nut. Additionally, peanut or nut products may be defined as products including peanut or nut proteins. Many possible types and configurations for the sensor are conceivable, including at least one array. Other examples of technology and/or sensors include, but are not limited to chemiresistant sensors, capillary electrophoretic sensors, optical microsensor arrays, surface enhanced raman spectroscopy (SERS), diode lasers, selected ion flow tubes, mass spectrometry, infrared spectrometry, colorimetric tubes, infrared spectroscopy, conductive-polymer gas-sensors (chemoresistors), polymerized crystalline colloidal arrays, responsive polymer-based sensors, nanotechnology, carbon nanotube technology, or molecular harp technology, a spectrophotometer, or other optical sensor.

It will be appreciated that the lists of above-mentioned components are not meant to be exclusive, and it is contemplated that a wide variety of other components may also be detected. It is contemplated that the sensor 710 may be configured to determine a concentration of at least one compound in the portioned foodstuff. In one embodiment, the sensor 710 may be configured to determine the concentration of one or more compounds on at least one of a per-mass basis, a per-volume basis, or a per-weight basis.

The sensor 710 is coupled to a reporter 712 for reporting information concerning one or more compounds detected by the sensor 710. The reporter 712 may be configured to report the information to one or more users or to a medical practitioner. The reporter 712 may comprise a memory 714 for storing information concerning the one or more compounds detected by the sensor 710. The memory 714 may comprise one or more of a flash memory, a random access memory (RAM), or a read-only memory (ROM). The reporter 712 may provide one or more of an audio signal, a tactile signal, or a visual signal for reporting the information concerning the one or more compounds. For instance, the reporter 712 may be configured with a display 716 (e.g., an LCD screen) for delivering one or more visual signals to the user or to a medical practitioner indicating the information. It is understood that audio signals, tactile signals, visual signals, or a combination of such signals may be utilized by the reporter 712.

The reporter 712 may further comprise a transmitter 718 for transmitting information concerning one or more compounds detected by the sensor 710 to a remote device. The transmitter 718 may utilize various communication technologies for data transmission. Such technologies may include, but are not limited to, radio transmission, Bluetooth transmission, Wi-Fi technology, infrared, and other wireless communication technologies. The remote device receiving the information may be utilized for various purposes. In one embodiment, the transmitter 718 may transmit the information to a remote display 720. The remote display 720 may be, for example, an external monitor capable of displaying the information to the user or a medical practitioner. In another embodiment, the transmitter 718 may transmit the information to a remote storage device 722. The remote storage device 722 may be, for example, a computer hard drive for Logging daily consumption records for the user.

It is contemplated that the device 700 may comprise detector 220 for detecting a portion size for the portioned foodstuff for consumption by one or more users (as previously described). The detector 220 may be coupled with processor 222 for determining a cumulative amount of one or more compounds based upon the portion size and the concentration of the compounds (as previously described). In one embodiment, the cumulative amount of one or more compounds may be calculated by multiplying the concentration of the compounds by the portion size. For example, if the sensor 710 determines the concentration of fat in the foodstuff is 5%, the cumulative amount of fat contained in a portioned foodstuff having portion size of 300 g by weight may be calculated by multiplying 300 g by 5%, resulting in 60 g of cumulative amount of fat.

It is understood that the cumulative amount of one or more compounds may be calculated utilizing a positively accumulated portion size. For example, a user may separate a first portion comprising a quantity of food having a first portion size of 20 g from a remaining portion of foodstuff. Then, the user may separate a second portion comprising a quantity of food having a second portion size of 40 g from the remaining portion of foodstuff. The processor 222 may determine the amount of fat contained in the first portion to be 1 g, and the mount of fat contained in the second portion to be 2 g. The processor 222 may then add the amount of fat in the first portion and the amount of fat in the second portion for a cumulative amount of one or more compounds comprising 3 g of fat. It is also understood that the cumulative amount of one or more compounds may be calculated utilizing a negatively accumulated portion size. In the above example, the processor 222 may subtract the amount of fat in the first portion of 1 g and the amount of fat in the second portion of 2 g from a starting amount (such as 50 g of fat), which may result a balance of 47 g of fat.

The reporter 712 may be configured to report when the cumulative amount of one or more compounds has reached a target amount. In one embodiment, the reporter 712 may comprise an alarm 724 for alerting the user when the target amount is reached. For example, the user may configure the target amount of fat to be 100 g by weight. Thus, the alarm 724 may alert the user once the cumulative amount of fat reaches or exceeds the target amount of 100 g. Such alert may be in forms of an audio alert, a tactile alert, a visual alert, or a combination of such alerts.

It is contemplated that the device 700 may comprise comparator 248 for comparing the cumulative amount of one or more compounds to a target amount or a goal amount (as previously described). In one embodiment, a comparison result (a representation of the comparison) may be reported on a display. In another embodiment, a transmitter may be utilized to transmit the representation of the comparison to a remote device. In still another embodiment, an alarm may alert the user or a medical practitioner regarding the comparison; for example, when the cumulative amount of one or more compounds approaches the target amount or the goal amount. It is also contemplated that the device 700 may further comprise a second device for portioning the foodstuff. The second device for portioning the foodstuff may be configured as device 200 or device 500 as previously described.

Figure 8:
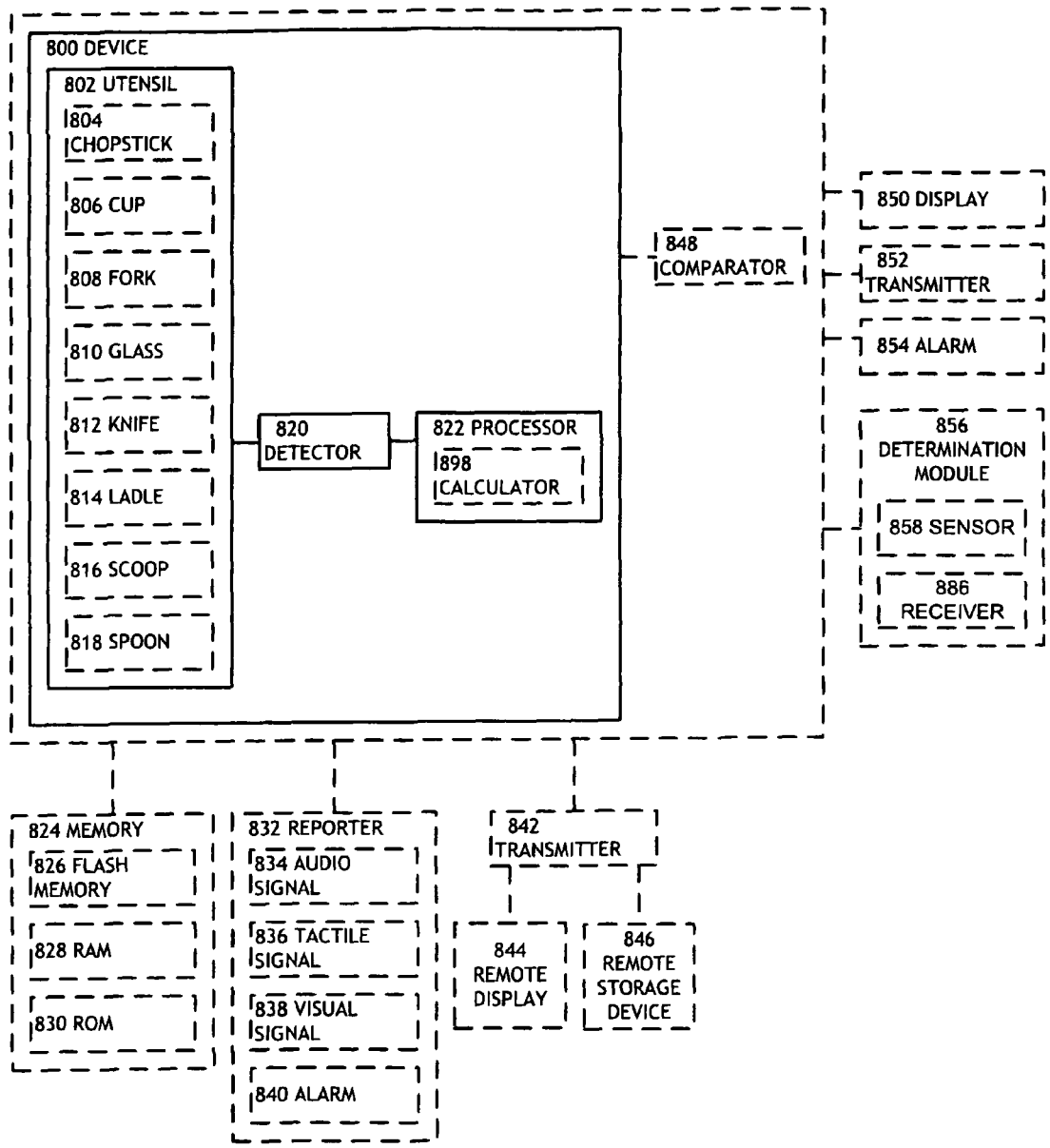
FIG. 8 is a schematic of another device for portioning a foodstuff.

Referring now to FIG. 8, a device 800 for portioning the foodstuff 100 (FIG. 1) is described. The device 800 includes an eating/serving utensil 802 for portioning the foodstuff into the first portion 102 (FIG. 1) and the second portion 106 (FIG. 1). The utensil 802 may comprise an eating instrument/implement that goes in the mouth. The utensil 802 may comprise one or more of a chopstick 804, a cup 806, a fork 808, a glass 810, a knife 812, a ladle 814, a scoop 816, or a spoon 818. The utensil 802 is coupled to a detector 820 for detecting a first nutritional content for the first portion and detecting a second nutritional content for the second portion. In one embodiment, the detector 820 may detect nutritional content of a portioned foodstuff utilizing one or more of a mass sensor, a volume sensor, or a weight sensor. It is contemplated that the detector 820 may comprise additional sensors, including, but not limited to, at least one of a calorimeter, a conductivity sensor, an electrical lead, an enzymatic sensor, a biosensor, a chemical sensor, a microchip sensor, an Enzyme-Linked Assay sensor (e.g., an Enzyme-Linked Immunosorbent Assay (ELISA) sensor), an infrared (IR) spectroscopy sensor, a Nuclear Magnetic Resonance (NMR) sensor, an optical sensor, a permittivity sensor, a gas sensor, a Radio Frequency (RF) sensor, an electronic nose sensor, an electronic tongue sensor, a multi-frequency RF sensor, a cantilever sensor, an acoustic wave sensor, a piezoelectric sensor, a responsive polymer-based sensor, a quartz microbalance sensor, a metal oxide sensor, an X-ray Fluorescence (XRF) sensor, a nucleic acid-based sensor (e.g., a DNA-, RNA-, or aptamer-based sensor), or a regenerable sensor, as well as other types of sensors capable of determining/detecting nutritional content of foodstuff.

The detector 820 is coupled to a processor 822 for determining a cumulative amount of nutritional content for the portioned foodstuff based upon the first nutritional content and the second nutritional content. For instance, a user may separate a first portion from a remaining portion of foodstuff. The first portion may comprise a quantity of food having a first nutritional content of 30 calories. Then, the user may separate a second portion from the remaining portion of foodstuff. The second portion may comprise a second quantity of food having a second nutritional content of 40 calories. The processor 822 may add the first nutritional content of 30 calories to the second nutritional content of 40 calories for a cumulative amount of nutritional content totaling 70 calories. In this manner, the processor 822 may be utilized to provide a positive accumulation of nutritional content for foodstuff.

In another example, a user may separate a first portion comprising a quantity of food having a first nutritional content of 20 calories from a remaining portion of foodstuff. Then, the user may separate a second portion comprising a quantity of food having a second nutritional content of 35 calories from the remaining portion of foodstuff. The processor 822 may subtract the first nutritional content of 20 calories and the second nutritional content of 35 calories from a starting amount (such as 120 calories) for a cumulative amount of nutritional content comprising 55 calories, which may be subtracted from the 120 calories, leaving a balance of 65 calories. In this manner, the processor 822 may be utilized to provide a negative accumulation of nutritional content for foodstuff.

The device 800 may comprise a determination module 856 for determining a nutritional parameter for the nutritional content. In one embodiment, the determination module 856 may be configured to determine an energy density for the nutritional content. More specifically, the energy density for the nutritional content may be determined in terms of a calorie density. In another embodiment, the determination module 856 may be configured to determine a component concentration for the nutritional content. The determination module 856 for determining the component concentration may be configured for determining at least one of a carbohydrate, a monosaccharide, a disaccharide, an oligosaccharide, a polysaccharide, a cellulose component, a fiber component, a sugar component, a dairy component, a fat, a saturated fat, an unsaturated fat, a polyunsaturated fat, a trans fat, a cholesterol component, a lipoprotein, a mineral, a peanut component, a protein, a salt, a triglyceride, or a vitamin. It will be appreciated that this list of components is not meant to be exclusive, and it is contemplated that a wide variety of other ingredients in various concentrations may also be detected. In still another embodiment, the determination module 856 may be configured to determine the nutritional parameter on at least one of a per-mass basis, a per-volume basis, or a per-weight basis.

The determination module 856 for determining the nutritional parameter for the nutritional content may comprise a sensor 858 for measuring the nutritional parameter for the nutritional content. The sensor 858 may comprise at least on of a calorimeter, a conductivity sensor, an electrical lead, an enzymatic sensor, a biosensor, a chemical sensor, a microchip sensor, an Enzyme-Linked Assay sensor (e.g., an Enzyme-Linked Immunosorbent Assay (ELISA) sensor), an infrared (IR) spectroscopy sensor, a Nuclear Magnetic Resonance (NMR) sensor, an optical sensor, a permittivity sensor, a gas sensor, a Radio Frequency (RF) sensor, an electronic nose sensor, an electronic tongue sensor, a multi-frequency RF sensor, a cantilever sensor, an acoustic wave sensor, a piezo-electric sensor, a responsive polymer-based sensor, a quartz microbalance sensor, a metal oxide sensor, an X-ray Fluorescence (XRF) sensor, a nucleic acid-based sensor (e.g., a DNA-, RNA-, or aptamer-based sensor), or a regenerable sensor. For example, a calorimeter may be utilized for measuring a calorie density for the nutritional content. In another example, a biosensor may be utilized for detecting/measuring a peanut component in the foodstuff.

The determination module 856 for determining the nutritional parameter for the nutritional content may also comprise a receiver 886 for receiving the nutritional parameter for the nutritional content. The receiver 886 may comprise at least one of a barcode reader, a database, a label reader, a meal-specific association, or a user input. For instance, a container of the foodstuff may comprise a barcode with one or more nutritional parameters embedded in the barcode information or associated with the barcode (e.g., a pre-packaged foodstuff may include a tray having a barcode). The receiver 886 comprising a barcode reader may be configured to read a nutritional parameter embedded in the barcode information. Alternatively, the determination module may be configured to look up a nutritional parameter by retrieving data indicated by the barcode. For example, a database or a look-up table may be used to determine a nutritional parameter for an identified foodstuff. In another example, the receiver 886 may be configured to receive one or more user inputs specifying the nutritional parameter of the nutritional content.

It is contemplated that the device 800 may comprise a memory 824 for storing the cumulative amount of nutritional content determined by the processor 822. The memory 824 may comprise one or more of a flash memory 826, a random access memory (RAM) 828, or a read-only memory (ROM) 830. The processor 822 may access or update the cumulative amount of nutritional content stored in the memory 824 during portioning operations performed by the device 800. For example, as the user separates the second portion from the remaining portion of foodstuff, the processor 822 may retrieve the cumulative amount of nutritional content currently stored in the memory 826. The processor 822 may then determine a new cumulative amount based on the cumulative amount of nutritional content retrieved from the memory 826 and the second nutritional content of the second portion. The processor 822 may update the cumulative amount of nutritional content stored in the memory 826 to reflect the new cumulative amount determined.

The device 800 may comprise a reporter 832 for reporting the cumulative amount of nutritional content determined by the processor 822. The reporter 832 may provide one or more of an audio signal 834, a tactile signal 836, or a visual signal 838. For instance, the reporter 832 may be configured with a display device (e.g., an LCD screen) for delivering one or more visual signals 838 to the user indicating the cumulative amount of nutritional content consumed by the user. It is understood that audio signals, tactile signals, visual signals, or a combination of such signals may be utilized by the reporter 832. In one embodiment, an LCD screen may be configured to provide information about the amount of nutritional content, such as a smiley face in the case of a desirable quantity that has been ingested. In another embodiment, a speaker may be configured to provide one or more tones, such as a warning signal/alarm in the case of an undesirable quantity of ingested nutritional content.

The reporter 832 may be configured to report when the cumulative amount of nutritional content has reached a target amount. In one embodiment, the reporter 832 may comprise an alarm 840 for alerting the user when the target amount is reached. For example, the user may configure the target amount to be 400 calories. Thus, the alarm 840 may alert the user once the cumulative amount of nutritional content determined by the processor 822 reaches or exceeds the target amount of 400 calories. An alert may be in the form of an audio alert, a tactile alert, a visual alert, or a combination of such alerts. In another example, the user may configure the target amount to be 50 g of fat. Thus, the alarm 840 may alert the user once the nutritional content determined by the processor 222 reaches or exceeds the target amount of 50 g of fat.

The device 800 may further comprise a transmitter 842 for transmitting the cumulative amount of nutritional content to a remote device. The transmitter 842 may utilize various communication technologies for data transmission. Such technologies may include, but are not limited to, radio transmission, Bluetooth transmission, Wi-Fi technology, infrared, and other wireless communication technologies. The remote device receiving the cumulative amount of nutritional content may be utilized for various purposes. In one embodiment, the transmitter 842 may transmit the cumulative amount of nutritional content to a remote display 844. The remote display 844 may be, for example, an external monitor capable of displaying information comprising the cumulative amount of nutritional content. In another embodiment, the transmitter 842 may transmit the cumulative amount of nutritional content to a remote storage device 846. The remote storage device 846 may be, for example, a computer hard drive for logging daily consumption records for the user.

The device 800 may also comprise a comparator 848 for comparing the cumulative amount of nutritional content to a target amount or a goat amount. For instance, the comparator 848 may compare the cumulative amount of nutritional content against the target amount when the second portion is separated from the remaining foodstuff (e.g., when the user imbibes a subsequent portion from the remaining foodstuff). In one embodiment, a comparison result (a representation of the comparison) may be reported on a display 850. In another embodiment, a transmitter 852 may be utilized to transmit the representation of the comparison to a remote device. In still another embodiment, an alarm 854 may alert the user regarding the comparison; for example, when the cumulative amount of nutritional content approaches the target amount or the goal amount.

Figure 9:
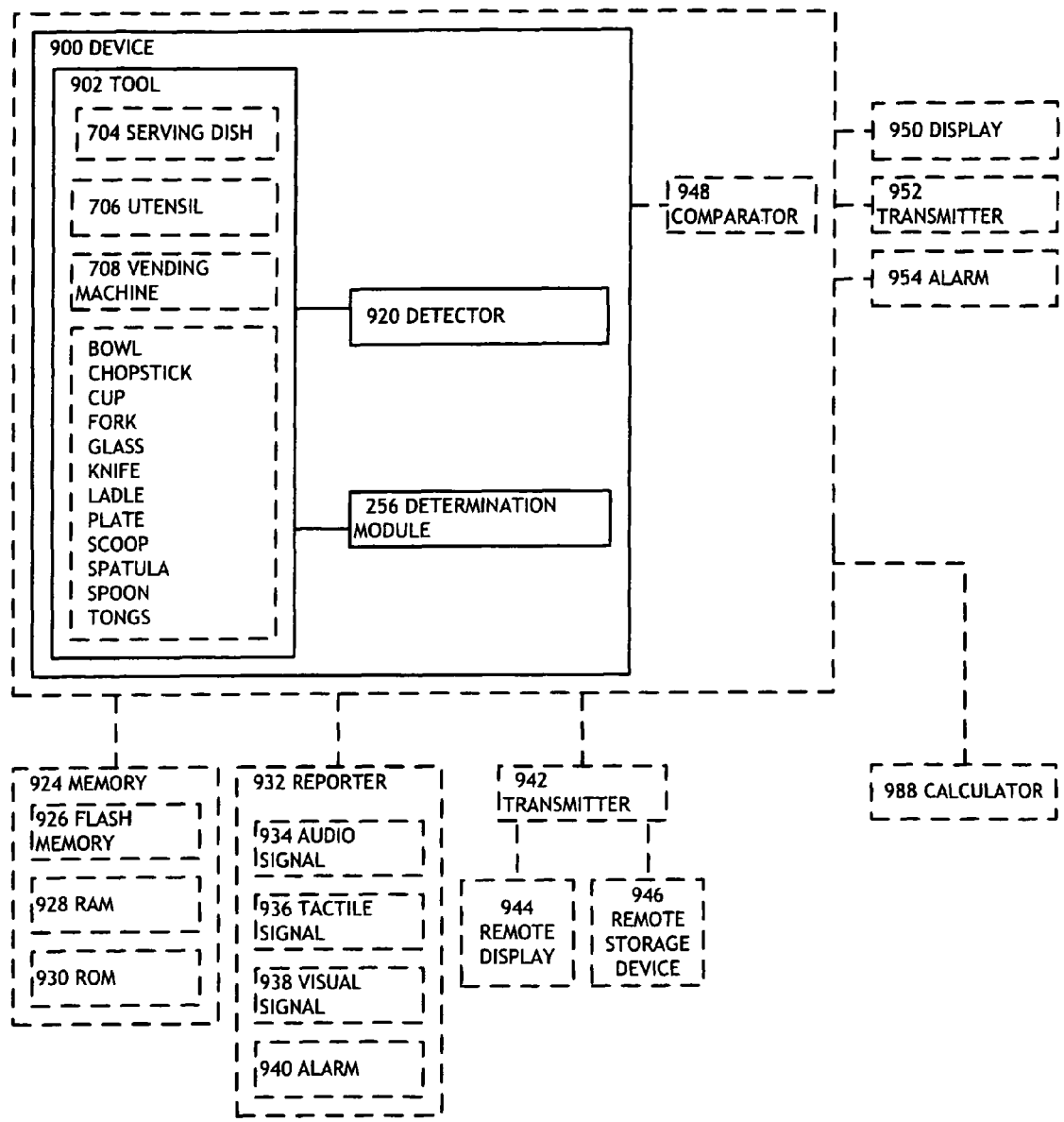
FIG. 9 is a schematic of another device for portioning a foodstuff.

Referring now to FIG. 9, a device 900 for presenting a portioned foodstuff is described. The device 900 includes a tool 902 for presenting the portioned foodstuff for consumption by at least one user. The tool 902 may comprise a container for presenting/serving the foodstuff or an eating instrument/implement that goes in the mouth. The tool 902 may comprise one or more of a serving dish 904, a utensil 906, or a vending machine 908. For example, the tool 902 may comprise one or more of a bowl, a chopstick, a cup, a fork, a glass, a knife, a ladle, a plate, a scoop, a spatula, a spoon, or tongs. The tool 902 is coupled to a detector 920 for detecting a portion size for the portioned foodstuff. The detector 920 may comprise an onboard mass sensor, volume sensor, or weight sensor for detecting the portion size by mass, volume, or weight, respectively. The tool 902 is also coupled to determination module 256 for determining a nutritional parameter for the portioned foodstuff (as previously described).

It is contemplated that the device 900 may comprise a calculator 988 for calculating a nutritional content for the portioned foodstuff. In one embodiment, the nutritional content may be calculated by the calculator 988 utilizing the nutritional parameter determined by the determination module 256 for the portioned foodstuff and the portion size for the portioned foodstuff determined by the detector 920. For instance, the nutritional content may be calculated based on the energy density determined by the determination module 256 for the portioned foodstuff and the portion size for the portioned foodstuff. If the energy density determined by the determination module 256 for the portioned foodstuff is, for example, 5 calories per 1 g, and the portion size for the foodstuff contained in the tool 902 is 50 g, the calculator 988 may calculate the nutritional content in terms of calorie density as 250 calories. In another example, the nutritional content may be calculated based on the component concentration determined by the determination module 256 for the portioned foodstuff and the portion size for the portioned foodstuff.

The device 900 may comprise a memory 924 for storing the portion size or the nutritional content of the portioned foodstuff. The memory 924 may comprise one or more of a flash memory 926, a random access memory (RAM) 928, or a read-only memory (ROM) 930. The portion size or the nutritional content of the portioned foodstuff stored in the memory 924 may be accessed or updated by the device 900 based on the portioned foodstuff contained in the tool 902. The device 900 may also comprise a reporter 932 for reporting the portion size or the nutritional content of the portioned foodstuff. The reporter 932 may provide one or more of an audio signal 934, a tactile signal 936, or a visual signal 938. For instance, the reporter 932 may be configured with a display device (e.g., an LCD screen) for delivering one or more visual signals 938 to the user indicating the portion size or the nutritional content of the portioned foodstuff contained in the tool 902. It is understood that audio signals, tactile signals, visual signals, or a combination of such signals may be utilized by the reporter 932.

The reporter 932 may be configured to report when the portion size or the nutritional content of the portioned foodstuff has reached a target amount. In one embodiment, the reporter 932 may comprise an alarm 940 for alerting the user when the target amount is reached. For example, the user may configure the target amount to be 500 g by weight. Thus, the alarm 240 may alert the user once the portion size of the portioned foodstuff reaches or exceeds the target amount of 500 g. An alert may be in forms of an audio alert, a tactile alert, a visual alert, or a combination of such alerts.

The device 900 may further comprise a transmitter 942 for transmitting the portion size or the nutritional content of the portioned foodstuff to a remote device. The transmitter 942 may utilize various communication technologies for data transmission. Such technologies may include, but are not limited to, radio transmission, Bluetooth transmission, Wi-Fi technology, infrared, and other wireless communication technologies. The remote device receiving the portion size or the nutritional content of the portioned foodstuff may be utilized for various purposes. In one embodiment, the transmitter 942 may transmit the portion size or the nutritional content of the portioned foodstuff to a remote display 944. The remote display 944 may be, for example, an external monitor capable of displaying information comprising the portion size or the nutritional content of the portioned foodstuff. In another embodiment, the transmitter 942 may transmit the portion size or the nutritional content of the portioned foodstuff to a remote storage device 946. The remote storage device 946 may be, for example, a computer hard drive for logging daily consumption records for the user.

The device 900 may also comprise a comparator 948 for comparing the portion size or the nutritional content of the portioned foodstuff to a target amount or a goal amount. In one embodiment, a comparison result (a representation of the comparison) may be reported on a display 950. In another embodiment, a transmitter 952 may be utilized to transmit the representation of the comparison to a remote device. In still another embodiment, an alarm 954 may alert the user regarding the comparison; for example, when the portion size or the nutritional content of the portioned foodstuff approaches the target amount or the goal amount.

Figure 10:
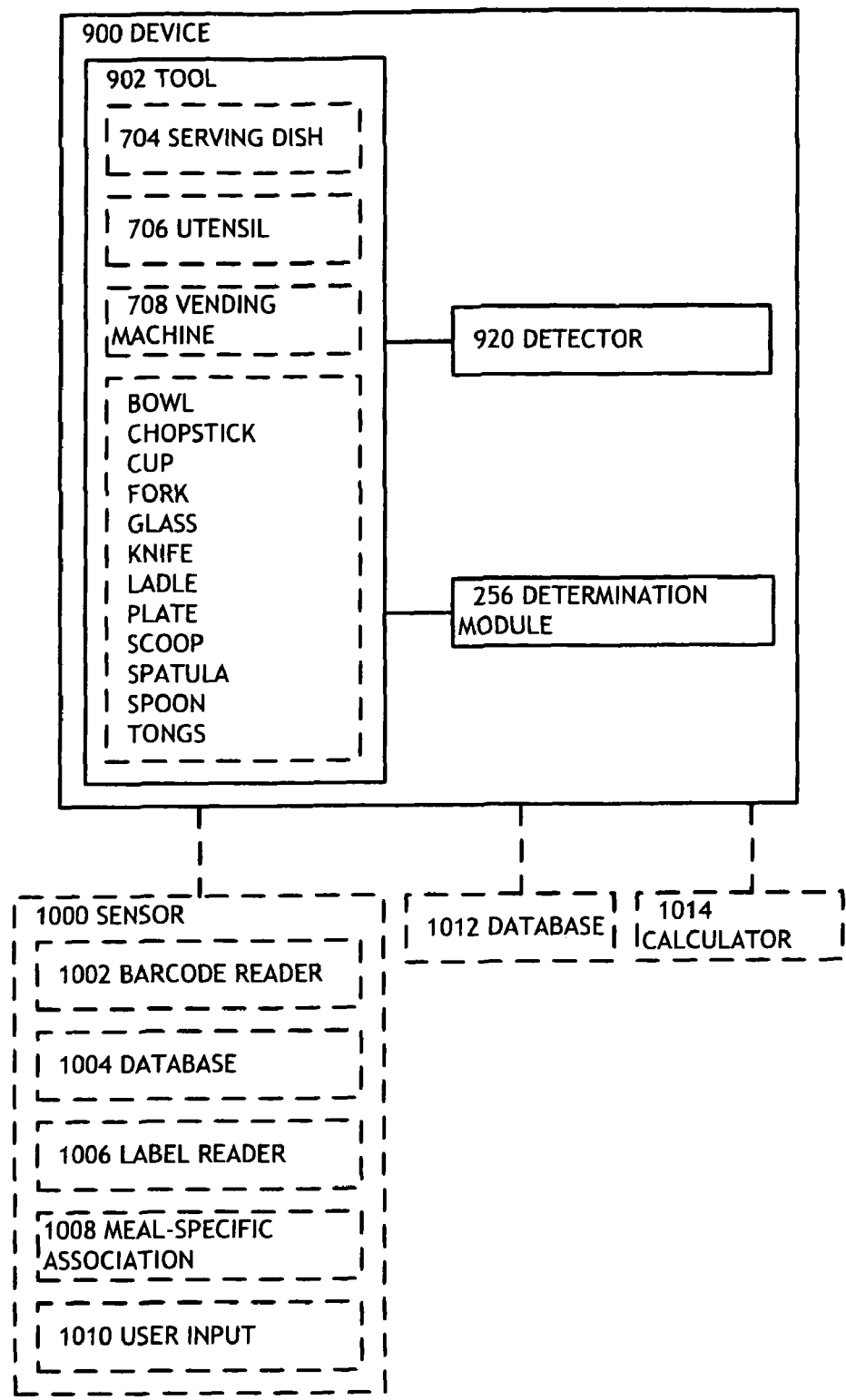
FIG. 10 is another schematic of the device illustrated in FIG. 9.

Referring now to FIG. 10, the device 900 may comprise a sensor 1000, a database 1012, and a calculator 1014. The sensor 1000 may be utilized for determining a type of the portioned foodstuff. The sensor 1000 may comprise at least one of a barcode reader 1002, a database 1004, a label reader 1006, a meal-specific association 1008, or a user input 1010. For instance, a container of foodstuff may comprise a barcode indicating the type of the foodstuff (e.g., a fruit, a vegetable, or a meat). The sensor 1000 comprising a barcode reader 1002 may be configured to read the barcode and determine the type of the foodstuff. Once the type of the foodstuff is determined, the device 900 may refer to the database 1012 to obtain a stored nutritional parameter for this type of foodstuff. For example, if the sensor 1000 determines that the portioned foodstuff is or contains banana, the device 900 may then obtain the stored nutritional parameter for banana from the database 1012. The calculator 1014 may be utilized for calculating a nutritional content for the portioned foodstuff utilizing the stored nutritional parameter for the portioned foodstuff and the portion size of the portioned foodstuff. In the above example, the calculator 1014 may calculate the nutritional content for the banana based on the stored nutritional parameter obtained from the database 1012 and the portion size for the foodstuff contained in the tool 902.

It is contemplated that the detectors and sensors depicted in the present disclosure may be configured for detecting allergenic substances in foodstuff. For example, a biosensor sensor may be utilized for detecting/measuring a peanut component in foodstuff. Additional examples of detecting allergenic substances (e.g., caffeine, alcohol, formaldehyde, monosodium glutamate, sulfites, nitrates, among others) in foodstuff may be found in McKay, U.S. Pat. No. 5,824,554, which is incorporated herein by reference. The detectors and sensors depicted in the present disclosure may also be configured for measuring/monitoring content of particular substances. One example of monitoring sodium content of foodstuff may be found in Byrd, U.S. Pat. No. 4,918,391, which is incorporated herein by reference. Another example of detecting caffeine content of foodstuff may be found in Catania et al., U.S. Pat. No. 6,461,873, which is incorporated herein by reference. The detectors and sensors depicted in the present disclosure may be further configured for sensing spoilage of foodstuff utilizing food spoilage sensors. One example of sensing food spoilage may be found in Kelly et al., U.S. Pat. No. 6,593,142, and Kelly et al., U.S. Pat. No. 6,924,147, which are incorporated herein by reference.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in tight of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. A device, comprising:
    a utensil for portioning a foodstuff into a first portion and a second portion;
    a detector coupled to the utensil for detecting a first portion size for the first portion and detecting a second portion size for the second portion;
    a processor coupled to the detector for determining a cumulative amount of portioned foodstuff based upon the first portion size and the second portion size; and
    a sensor coupled to the utensil for directly contacting the portioned foodstuff and for sensing at least one ingredient of the portioned foodstuff.

2. The device of claim 1, wherein a utensil for portioning a foodstuff into a first portion and a second portion comprises:
    at least one of a chopstick, a cup, a fork, a glass, a knife, a ladle, a scoop, or a spoon.

3. The device of claim 1, wherein a detector coupled to the utensil for detecting a first portion size for the first portion and detecting a second portion size for the second portion comprises:
    a detector for detecting the first portion size for the first portion, wherein the first portion is sized by at least one of mass, volume, or weight.

4. The device of claim 1, wherein a processor coupled to the detector for determining a cumulative amount of portioned foodstuff based upon the first portion size and the second portion size comprises:
    a processor for adding the first portion size and the second portion size for a positive accumulation.

5. The device of claim 1, wherein a processor coupled to the detector for determining a cumulative amount of portioned foodstuff based upon the first portion size and the second portion size comprises:
    a processor for subtracting the first portion size and the second portion size for a negative accumulation.

6. The device of claim 1, further comprising:
    a memory for storing the cumulative amount of the portioned foodstuff.

7. The device of claim 6, wherein a memory for storing the cumulative amount of the portioned foodstuff comprises:
    at least one of flash memory, Random Access Memory (RAM), or Read Only Memory (ROM).

8. The device of claim 1, further comprising:
    a reporter for reporting the cumulative amount of the portioned foodstuff.

9. The device of claim 8, wherein a reporter for reporting the cumulative amount of the portioned foodstuff comprises:
    at least one of an audio signal, a tactile signal, or a visual signal.

10. The device of claim 1, further comprising:
    a reporter for reporting that the cumulative amount of the portioned foodstuff has reached a target amount.

11. The device of claim 10, wherein a reporter for reporting that the cumulative amount of the portioned foodstuff has reached a target amount comprises:
    an alarm for alerting a user when the target amount is reached.

12. The device of claim 1, further comprising:
    a transmitter for transmitting the cumulative amount of the portioned foodstuff.

13. The device of claim 12, wherein a transmitter for transmitting the cumulative amount of the portioned foodstuff comprises:
    a transmitter for transmitting the cumulative amount of the portioned foodstuff to a remote display.

14. The device of claim 12, wherein a transmitter for transmitting the cumulative amount of the portioned foodstuff comprises:
    a transmitter for transmitting the cumulative amount of the portioned foodstuff to a remote storage device.

15. The device of claim 1, further comprising:
    a comparator for comparing the cumulative amount of the portioned foodstuff to a target amount.

16. The device of claim 15, wherein a comparator for comparing the cumulative amount of the portioned foodstuff to a target amount comprises:
    a comparator for comparing the cumulative amount of the portioned foodstuff to a goal amount.

17. The device of claim 15, further comprising:
    a display for reporting a representation of the comparison.

18. The device of claim 15, further comprising:
    a transmitter for transmitting a representation of the comparison.

19. The device of claim 15, further comprising:
    an alarm for alerting a user to the comparison.

20. The device of claim 1, further comprising:
    a determination module for determining a nutritional parameter for the portioned foodstuff.

21. The device of claim 20, wherein a determination module for determining a nutritional parameter for the portioned foodstuff comprises:
    a determination module for determining an energy density for the portioned foodstuff.

22. The device of claim 21, wherein a determination module for determining an energy density for the portioned foodstuff comprises:
    a determination module for determining a calorie density for the portioned foodstuff.

23. The device of claim 20, wherein a determination module for determining a nutritional parameter for the portioned foodstuff comprises:
    a determination module for determining a component concentration of the at least one ingredient of the portioned foodstuff.

24. The device of claim 23, wherein a determination module for determining a component concentration of the at least one ingredient of the portioned foodstuff comprises:
    a determination module for determining a concentration of at least one of a carbohydrate, a monosaccharide, a disaccharide, an oligosaccharide, a polysaccharide, a cellulose component, a fiber component, a sugar component, a dairy component, a fat, a saturated fat, an unsaturated fat, a polyunsaturated fat, a trans fat, a cholesterol component, a lipoprotein, a mineral, a peanut component, a protein, a salt, a triglyceride, or a vitamin.

25. The device of claim 20, wherein a determination module for determining a nutritional parameter for the portioned foodstuff comprises:
a determination module for determining the nutritional parameter on at least one of a per-mass basis, a per-volume basis, or a per-weight basis.

26. The device of claim 1, wherein a sensor coupled to the utensil for directly contacting the portioned foodstuff and for sensing at least one ingredient of the portioned foodstuff comprises:
at least one of a calorimeter, a conductivity sensor, an electrical lead, an enzymatic sensor, a biosensor, a chemical sensor, a microchip sensor, an Enzyme-Linked Assay sensor, an infrared (IR) spectroscopy sensor, a Nuclear Magnetic Resonance (NMR) sensor, an optical sensor, a permittivity sensor, a gas sensor, a Radio Frequency (RF) sensor, an electronic nose sensor, an electronic tongue sensor, a multi-frequency RF sensor, a cantilever sensor, an acoustic wave sensor, a piezoelectric sensor, a responsive polymer-based sensor, a quartz microbalance sensor, a metal oxide sensor, an X-ray Fluorescence (XRF) sensor, a nucleic acid-based sensor, or a regenerable sensor.

27. The device of claim 1, wherein a processor coupled to the detector for determining a cumulative amount of portioned foodstuff based upon the first portion size and the second portion size comprises:
a calculator for calculating a nutritional content for the portioned foodstuff utilizing a nutritional parameter for the portioned foodstuff and the cumulative amount of the portioned foodstuff.

28. The device of claim 27, wherein a calculator for calculating a nutritional content for the portioned foodstuff utilizing a nutritional parameter for the portioned foodstuff and the cumulative amount of the portioned foodstuff comprises:
a calculator for calculating a nutritional content for the portioned foodstuff utilizing an energy density for the portioned foodstuff and the cumulative amount of the portioned foodstuff.

29. The device of claim 27, wherein a calculator for calculating a nutritional content for the portioned foodstuff utilizing a nutritional parameter for the portioned foodstuff and the cumulative amount of the portioned foodstuff comprises:
a calculator for calculating a nutritional content for the portioned foodstuff utilizing a component concentration of the at least one ingredient of the portioned foodstuff and the cumulative amount of the portioned foodstuff.

30. The device of claim 27, further comprising:
a memory for storing the nutritional content for the portioned foodstuff.

31. The device of claim 30, wherein a memory for storing the nutritional content for the portioned foodstuff comprises:
at least one of flash memory, Random Access Memory (RAM), or Read Only Memory (ROM).

32. The device of claim 27, further comprising:
a reporter for reporting the nutritional content for the portioned foodstuff.

33. The device of claim 32, wherein a reporter for reporting the nutritional content for the portioned foodstuff comprises:
at least one of an audio signal, a tactile signal, or a visual signal.

34. The device of claim 27, further comprising:
a reporter for reporting that the nutritional content of the portioned foodstuff has reached a target amount.

35. The device of claim 34, wherein a reporter for reporting that the nutritional content of the portioned foodstuff has reached a target amount comprises:
an alarm for alerting a user when the target amount is reached.

36. The device of claim 27, further comprising:
a transmitter for transmitting the nutritional content for the portioned foodstuff.

37. The device of claim 36, wherein a transmitter for transmitting the nutritional content for the portioned foodstuff comprises:
a transmitter for transmitting the nutritional content for the portioned foodstuff to a remote display.

38. The device of claim 36, wherein a transmitter for transmitting the nutritional content for the portioned foodstuff comprises:
a transmitter for transmitting the nutritional content for the portioned foodstuff to a remote storage device.

39. The device of claim 27, further comprising:
a comparator for comparing the nutritional content for the portioned foodstuff to a target amount.

40. The device of claim 39, wherein a comparator for comparing the nutritional content for the portioned foodstuff to a target amount comprises:
a comparator for comparing the nutritional content for the portioned foodstuff to a goal amount.

41. The device of claim 39, further comprising:
a display for reporting a representation of the comparison.

42. The device of claim 39, further comprising:
a transmitter for transmitting a representation of the comparison.

43. The device of claim 39, further comprising:
an alarm for alerting a user to the comparison.

44. The device of claim 1, further comprising:
a second sensor for determining a type of the portioned foodstuff;
a database for referencing the type of the portioned foodstuff against a stored nutritional parameter for the portioned foodstuff; and
a calculator for calculating a nutritional content for the portioned foodstuff utilizing the stored nutritional parameter for the portioned foodstuff and the cumulative amount of the portioned foodstuff.

45. The device of claim 44, wherein a second sensor for determining a type of the portioned foodstuff comprises:
at least one of a barcode reader, a database, a label reader, a meal-specific association, or a user input.

* * * * *